United States Patent
Zheng et al.

(10) Patent No.: US 10,127,470 B2
(45) Date of Patent: Nov. 13, 2018

(54) COMPUTERIZED METHOD AND APPARATUS FOR DETERMINING OBSTRUCTED PORTIONS OF DISPLAYED DIGITAL CONTENT

(71) Applicant: Alibaba Group Holding Limited, Grand Cayman (KY)

(72) Inventors: Qi Zheng, Hangzhou (CN); Yongpan Wang, Hangzhou (CN)

(73) Assignee: ALIBABA GROUP HOLDING LIMITED, Grand Cayman (KY)

(*) Notice: Subject to any disclaimer, the term of this patent is extended or adjusted under 35 U.S.C. 154(b) by 98 days.

(21) Appl. No.: 15/117,190

(22) PCT Filed: Feb. 2, 2015

(86) PCT No.: PCT/CN2015/072115
§ 371 (c)(1),
(2) Date: Oct. 28, 2016

(87) PCT Pub. No.: WO2015/120772
PCT Pub. Date: Aug. 20, 2015

(65) Prior Publication Data
US 2017/0039443 A1    Feb. 9, 2017

(30) Foreign Application Priority Data
Feb. 11, 2014    (CN) .......................... 2014 1 0047760

(51) Int. Cl.
*G06K 9/42* (2006.01)
*G06K 9/62* (2006.01)
(Continued)

(52) U.S. Cl.
CPC .......... *G06K 9/42* (2013.01); *G06F 17/30247* (2013.01); *G06F 19/00* (2013.01);
(Continued)

(58) Field of Classification Search
CPC ............. G06K 9/6267; G06K 9/00456; G06K 9/00664; G06K 9/4604; G06K 9/42;
(Continued)

(56) References Cited

U.S. PATENT DOCUMENTS

| | | | |
|---|---|---|---|
| 8,639,036 B1* | 1/2014 | Singer | G06K 9/6217 382/141 |
| 2009/0297024 A1* | 12/2009 | Dai | G06K 9/00456 382/165 |

FOREIGN PATENT DOCUMENTS

| | | |
|---|---|---|
| CN | 102799669 A | 11/2012 |
| CN | 102819566 A | 12/2012 |
| CN | 102842135 A | 12/2012 |

OTHER PUBLICATIONS

International Search Report to corresponding PCT Application No. PCT/CN2015/072115, dated Apr. 29, 2015.

* cited by examiner

*Primary Examiner* — Kim Vu
*Assistant Examiner* — Michael Vanchy, Jr.
(74) *Attorney, Agent, or Firm* — James J. DeCarlo; Greenberg Traurig, LLP

(57) ABSTRACT

Disclosed are systems and methods for improving interactions with and between computers in content communicating, rendering, generating, hosting and/or providing systems supported by or configured with computing devices, servers and/or platforms. The systems interact to improve the quality of data used in processing interactions between or among processors in such systems for determining obscured portions of displayed digital content. The disclosed method and apparatus involve acquiring and recording coordinates of each pixel in a digital image, and marking the pixels located at a boundary of the image as boundary pixels. The pixels located at a first region block are extracted and marked as (Continued)

obstruction pixels. An obstructed cutting space area corresponding to each pixel is determined based on positional relations of each pixel in the image. An image obstruction score is calculated based on the cutting space areas and utilized for rendering the pixels of the image.

19 Claims, 5 Drawing Sheets

(51) Int. Cl.
*G06F 17/30* (2006.01)
*G06K 9/46* (2006.01)
*G16H 50/30* (2018.01)
*G06F 19/00* (2018.01)
*G06K 9/34* (2006.01)
*G16H 50/20* (2018.01)

(52) U.S. Cl.
CPC .............. *G06F 19/321* (2013.01); *G06K 9/34* (2013.01); *G06K 9/4652* (2013.01); *G06K 9/6267* (2013.01); *G16H 50/30* (2018.01); *G16H 50/20* (2018.01)

(58) Field of Classification Search
CPC ... G06K 9/4652; G06T 7/00; G06F 17/30247; G06F 19/321; G06F 19/3431; G06F 19/345
See application file for complete search history.

COMPUTERIZED METHOD AND APPARATUS FOR DETERMINING OBSTRUCTED PORTIONS OF DISPLAYED DIGITAL CONTENT

CROSS-REFERENCE TO RELATED APPLICATIONS

This application claims the benefit of priority from Chinese Patent Application No. 201410047760.8, filed on Feb. 11, 2014 and PCT Application No. PCT/CN2015/072115, filed on Feb. 2, 2015, which are incorporated herein in their entirety by reference.

BACKGROUND

Field of the Disclosure

The present application relates to the technical field of computer communication, and in particular, to providing non-native functionality to devices, systems and platforms for determining obscured portions of displayed digital content by calculating an image score for obscured or obstructed portions of the digital image content.

Description of Related Art

With the recent developments in computer communication technologies, increasing numbers of merchants choose to sell products through shopping (e.g., e-commerce) websites. Products displayed by merchants on shopping websites generally employ real-shot (or digitally captured) images of a product; however, in many cases, some generated content is added on the product image for identifying brands, introducing products or propagating sales promotions. The generated content may include texts, trademarks, patterns, and the like. In general, the generated content for the product image is only auxiliary information associated with the product, playing a supporting role. Disadvantages will occur if the generated content does more than support the product, thereby affecting the visual display of the product body (e.g., the displayed digital content associated the actual product). For ease of description, the product image whose generated content does more than support, which obscures or obstructs the display of the product body, may be referred to as an obstructed (or obscured) image. By way of example, a conventional or existing method for calculating a product image obstruction score is as follows: acquiring a product image; extracting an obstruction region block from the product image, wherein the obstruction region block includes a text region block, a trademark region block and a pattern region block; calculating the number, area, position and color of the obstruction region block; and calculating the product image obstruction score according to the number, area, position and color of the obstruction region block.

As highlighted above, such existing methods calculate an obstruction score for a displayed image according to the number, area, position and color of the psoriasis region block. However, an obstruction score is not only related to an absolute position of the obstruction region block, but is also related to a relative position between the obstruction region blocks. Moreover, a simple summation of the number and the area of the obstructed region block cannot represent the severity of the obstruction within the position and color range. Therefore, the calculated product image obstructed score in the existing method is inaccurate, and whether the product image is an obstruction image and the severity of the obstruction cannot be accurately determined.

BRIEF SUMMARY

The present disclosure remedies the above identified technical problems in the art, inter alia, by providing a method and apparatus for calculating a product image obstruction score via the novel, computerized techniques discussed herein. According to some embodiments of the instant disclosure, a method is disclosed which includes: calculating an obstruction cutting space area corresponding to each pixel in the product image based on determined positional relations of each pixel in the product image, determined boundary pixels within the image, and identified obstruction pixels within the image; and calculating the product image obstruction score based on the obstruction cutting space areas corresponding to all the pixels in the product image (e.g., the pixel being an actual element of the product image reflecting the real condition of the product image). As evidenced from the disclosure herein, the accuracy of a product image obstruction score is improved from the implementations of the computerized method and apparatus discussed herein, as the obstruction score can more accurately reflect whether a product image is an obstructed image and the severity of such obstruction within the image.

In order to ensure an enjoyable and beneficial network shopping experience for a merchant and consumer, a product image obstruction score may be calculated, as discussed herein. As discussed herein, the obstruction score provides a quantified value or metric of how severely obstructed a product image is when displayed on an e-commerce site. Among other advantages, this can provide the merchant, system, administrator, platform or device the ability to determine whether the display of the product image is prohibited, which can be determined according to whether the product image is obstructed and how severe such obstruction is—as indicated by the value of the obstruction score.

According to some embodiments of the instant disclosure, a method is disclosed which includes:

acquiring a product image, recording coordinates of each pixel in the product image, and marking the pixels located at a boundary of the product image as boundary pixels;

extracting a first region block in the product image, and marking the pixels located at the first region block as obstructed pixels;

calculating an obstructed cutting space area corresponding to each pixel in the product image based on positional relations of each pixel in the product image with the boundary pixels, and with the obstructed pixels; and calculating the product image obstructed score based on the obstructed cutting space areas corresponding to all the pixels in the product image.

According to some embodiments, the method further includes extracting a first region block in the product image, where the pixels located at the first region block are marked as obstructed pixels. In some embodiments, such extraction includes:

extracting a first region block in the product image;

analyzing a color saliency of the first region block;

expanding the first region block to obtain the expanded first region block based on the color saliency magnitude of the first region block; and marking the pixels located at the expanded first region block as the obstructed pixels.

According to some embodiments, the method further includes calculating the obstructed cutting space area corresponding to each pixel in the product image based on positional relations of each pixel in the product image with the boundary pixels and with the obstructed pixels. In some embodiments, such calculation includes:

using each pixel in the product image respectively as current pixels;

determining whether the current pixels are the obstructed pixels;

taking the current pixel as a center and searching for the first obstructed pixels or the boundary pixels in a horizontally leftward direction, a horizontally rightward direction, a vertically upward direction and a vertically downward direction of the current pixels respectively, if the current pixels are not the obstructed pixels;

using the first obstructed pixels or the boundary pixels in the horizontally leftward direction, the horizontally rightward direction, the vertically upward direction and the vertically downward direction as left boundary points, right boundary points, upper boundary points, and lower boundary points of the current pixels respectively;

obtaining widths of the obstructed cutting space areas corresponding to the current pixels based on coordinates of the left boundary points and coordinates of the right boundary points;

obtaining heights of the obstructed cutting space areas corresponding to the current pixels based on coordinates of the upper boundary points and coordinates of the lower boundary points; and obtaining the obstructed cutting space area corresponding to the current pixels based on the widths and the heights of the obstructed cutting space areas corresponding to the current pixels.

According to some embodiments, the method further includes, after determining whether the current pixels are the obstructed pixels:

setting the obstructed cutting space areas corresponding to the current pixels to zero if the current pixels are the obstructed pixels.

In some embodiments, the steps of calculating the product image obstructed score based on the obstructed cutting space areas corresponding to all the pixels in the product image includes:

using the obstructed cutting space area corresponding to each pixel in the product image or a monotonically increasing function value (e.g., greater than zero) of the obstructed cutting space area corresponding to each pixel as a weight of each pixel in the product image; and calculating the product image obstructed score based on a value obtained by performing a weight summation and normalization to all the pixels in the product image.

In some embodiments, the steps of calculating the product image obstructed score based on a value obtained by performing a weight summation and normalization to all the pixels in the product image includes:

using the value obtained by performing a weight summation and normalization to all the pixels in the product image as the obstructed reference score of the product image; and obtaining the product image obstructed score based on the obstructed reference score and a preset representation of the obstructed score.

In some embodiments, after calculating the product image obstructed score, the method further includes:

comparing the calculated product image obstructed score with a preset obstructed determination threshold or an obstructed classification threshold; and determining or classifying an obstructed severity of the product image based on the comparison result.

In some embodiments, the first region block comprises at least one of the following: a text region block, a trademark region block, and a pattern region block.

According to some embodiments of the instant disclosure, an apparatus for calculating the product image obstructed score is disclosed, the apparatus includes:

an acquisition module, used for acquiring a product image, recording coordinates of each pixel in the product image, and marking the pixels located at a boundary of the product image as boundary pixels;

an extraction module, used for extracting a first region block in the product image and marking the pixels located at the first region block as the obstructed pixels, wherein the first region block comprises at least one of the following: a text region block, a trademark region block, and a pattern region block;

a first calculation module, used for calculating an obstructed cutting space area corresponding to each pixel in the product image based on positional relations of each pixel in the product image with the boundary pixels, and with the obstructed pixels; and a second calculation module, used for calculating the product image obstructed score based on the obstructed cutting space areas corresponding to all the pixels in the product image.

According to some embodiments, the extraction module includes:

an extraction unit, used for extracting a first region block in the product image;

an analysis unit, used for analyzing a color saliency of the first region block;

an expansion unit, used for expanding the first region block to obtain the expanded first region block based on the color saliency magnitude of the first region block; and a marking unit, used for marking the pixels located at the expanded first region block as the obstructed pixels.

In some embodiments, the first calculation module includes:

a first processing unit, used for using each pixel in the product image respectively as a current pixel;

a determination unit, used for determining whether the current pixels are the obstructed pixels;

a searching unit, used for taking the current pixel as a center, searching for the first obstructed pixels or the boundary pixels in a horizontally leftward direction, a horizontally rightward direction, a vertically upward direction, and a vertically downward direction of the current pixels respectively, if the current pixels are not the obstructed pixels;

a second processing unit, used for using the first obstructed pixels or the boundary pixels in the horizontally leftward direction, the horizontally rightward direction, the vertically upward direction and the vertically downward direction as left boundary points, right boundary points, upper boundary points, and lower boundary points of the current pixels respectively;

a width acquisition unit, used for obtaining widths of the obstructed cutting space areas corresponding to the current pixels based on the coordinates of the left boundary points and the coordinates of the right boundary points;

a height acquisition unit, used for obtaining heights of the obstructed cutting space areas corresponding to the current pixels based on the coordinates of the upper boundary points and the coordinates of the lower boundary points; and an area acquisition unit, used for obtaining the obstructed cutting space areas corresponding to the current pixels based on the widths and the heights of the obstructed cutting space areas corresponding to the current pixels.

In some embodiments, the first calculation module further includes:

a setting unit, used for setting the obstructed cutting space areas corresponding to the current pixels to zero if the current pixels are the v pixels.

In some embodiments, the second calculation module includes:

a weight acquisition unit, used for using the obstructed cutting space area corresponding to each pixel in the product image or a monotonically increasing function value (e.g., greater than zero) of the obstructed cutting space area corresponding to each pixel as a weight of each pixel in the product image; and a score acquisition unit, used for calculating the product image obstructed score based on a value obtained by performing a weight summation and normalization to all the pixels in the product image.

In some embodiments, the score acquisition unit includes:

a reference score acquisition subunit, used for using the value obtained by performing a weight summation and normalization to all the pixels in the product image as the obstructed reference score of the product image; and a score obtaining subunit, used for obtaining the product image obstructed score based on the obstructed reference score and a preset representation of the obstructed score.

In some embodiments, the apparatus further includes:

a comparison module, used for comparing the calculated product image obstructed score with a preset obstructed determination threshold or an obstructed classification threshold; and a determination or classification module, used for determining or classifying an obstructed severity of the product image based on the comparison result.

In some embodiments, the first region block comprises at least one of the following: a text region block, a trademark region block, and a pattern region block.

Compared with the prior art, the present application can obtain the following technical effects:

By calculating an obstructed cutting space area corresponding to each pixel in the product image based on positional relations of each pixel in the product image with the boundary pixels and with the obstructed pixels, and by calculating a product image obstructed score based on the obstructed cutting space areas corresponding to all the pixels in the product image (e.g., the pixel being an actual element of the product image reflecting the real condition of the product image), the accuracy of the product image obstructed score is improved, and it can more accurately determine whether a product image is an obstructed image, along with the severity of the obstruction. In some embodiments, the first region block is expanded to obtain the expanded first region block based on the color saliency magnitude of the first region block, such that a more accurate first region block can be obtained, thereby further improving the accuracy of the product image obstructed score.

Certainly, any product of the disclosed and understood embodiments of the present disclosure does need to achieve all of the above described technical effects at the same time.

In accordance with one or more embodiments, a non-transitory computer-readable storage medium is provided, the non-transitory computer-readable storage medium tangibly storing thereon, or having tangibly encoded thereon, computer readable instructions that when executed cause at least one processor to perform a method as discussed herein.

In accordance with one or more embodiments, a system is provided that comprises one or more computing devices (also referred to as a "device") configured to provide functionality in accordance with such embodiments. In accordance with one or more embodiments, functionality is embodied in steps of a method performed by at least one computing device. In accordance with one or more embodiments, program code (or program logic or computer-executable instructions) is executed by a processor(s) of a computing device to implement functionality in accordance with one or more such embodiments is embodied in, by and/or on a non-transitory computer-readable medium.

BRIEF DESCRIPTION OF THE DRAWINGS

The foregoing and other objects, features, and advantages of the disclosure will be apparent from the following description of embodiments as illustrated in the accompanying drawings, in which reference characters refer to the same parts throughout the various views. The drawings are not necessarily to scale, emphasis instead being placed upon illustrating principles of the disclosure.

DETAILED DESCRIPTION

Figure 1:
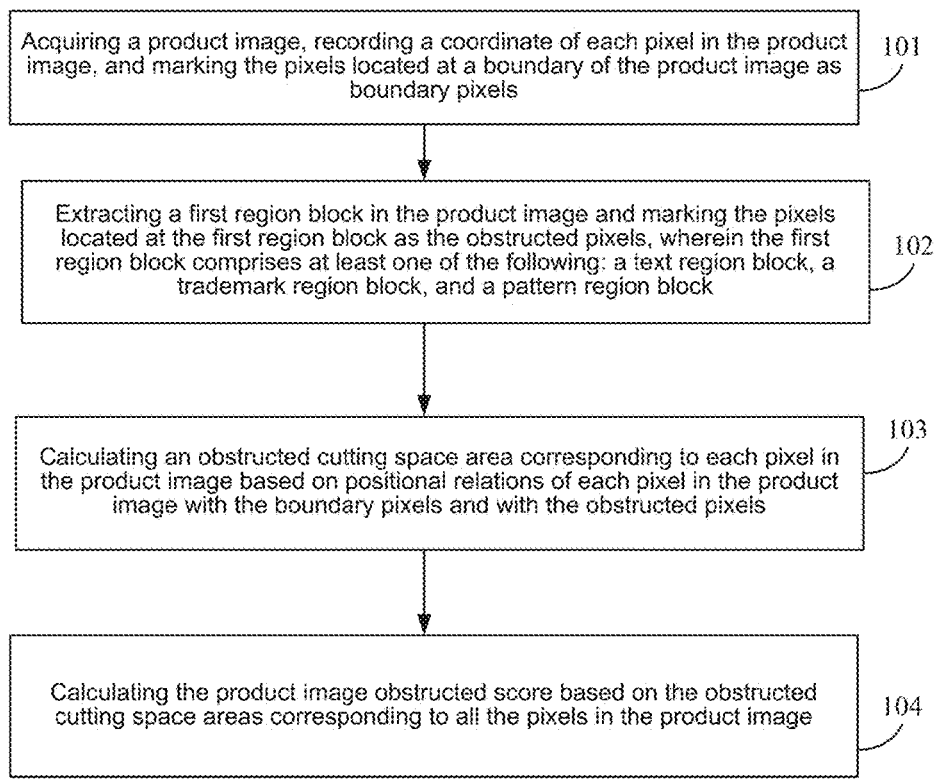
FIG. 1 is a flow diagram of a method for calculating a product image obstruction score according to some embodiments of the present disclosure.

The present disclosure will now be described more fully hereinafter with reference to the accompanying drawings, which form a part hereof, and which show, by way of illustration, specific example embodiments. Subject matter may, however, be embodied in a variety of different forms and, therefore, covered or claimed subject matter is intended to be construed as not being limited to any example embodiments set forth herein; example embodiments are provided merely to be illustrative. Likewise, a reasonably broad scope for claimed or covered subject matter is intended. Among other things, for example, subject matter may be embodied as methods, devices, components, or systems. Accordingly, embodiments may, for example, take the form of hardware, software, firmware or any combination thereof (other than software per se). The following detailed description is, therefore, not intended to be taken in a limiting sense.

Throughout the specification and claims, terms may have nuanced meanings suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter include combinations of example embodiments in whole or in part.

In general, terminology may be understood at least in part from usage in context. For example, terms, such as "and", "or", or "and/or," as used herein may include a variety of meanings that may depend at least in part upon the context in which such terms are used. Typically, "or" if used to associate a list, such as A, B or C, is intended to mean A, B, and C, here used in the inclusive sense, as well as A, B or C, here used in the exclusive sense. In addition, the term "one or more" as used herein, depending at least in part upon context, may be used to describe any feature, structure, or characteristic in a singular sense or may be used to describe combinations of features, structures or characteristics in a plural sense. Similarly, terms, such as "a," "an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

The present disclosure is described below with reference to block diagrams and operational illustrations of methods and devices. It is understood that each block of the block diagrams or operational illustrations, and combinations of blocks in the block diagrams or operational illustrations, can be implemented by means of analog or digital hardware and computer program instructions. These computer program instructions can be provided to a processor of a general purpose computer to alter its function as detailed herein, a special purpose computer, ASIC, or other programmable data processing apparatus, such that the instructions, which executed via the processor of the computer or other programmable data processing apparatus, implement the functions/acts specified in the block diagrams or operational block or blocks. In some alternate implementations, the functions/acts noted in the blocks can occur out of the order noted in the operational illustrations. For example, two blocks shown in succession can in fact be executed substantially concurrently or the blocks can sometimes be executed in the reverse order, depending upon the functionality/acts involved.

These computer program instructions can be provided to a processor of a general purpose computer to alter its function, a special purpose computer, ASIC, or other programmable data processing apparatus, such that the instructions, which execute via the processor of the computer or other programmable data processing apparatus, implement the functions/acts specified in the block diagrams or operational block or blocks.

For purposes of this disclosure, a typical configuration of a computing device includes, but is not limited to, one or more processors (CPUs), input/output interfaces, networking interfaces and a storage. A computing device may be capable of sending or receiving signals, such as via a wired or wireless network, or may be capable of processing or storing signals, such as in memory as physical memory states, and may, therefore, operate as a server. Thus, devices capable of operating as a server may include, as examples, dedicated rack-mounted servers, desktop computers, laptop computers, set top boxes, integrated devices combining various features, such as two or more features of the foregoing devices, or the like. Servers may vary widely in configuration or capabilities, but generally a server may include one or more central processing units and memory. A server may also include one or more mass storage devices, one or more power supplies, one or more wired or wireless network interfaces, one or more input/output interfaces, or one or more operating systems, such as Windows Server, Mac OS X, Unix, Linux, FreeBSD, or the like.

For purposes of this disclosure, a computing device (or client or consumer or user) device is capable of sending or receiving signals, such as via a wired or a wireless network. A computing device may, for example, include a desktop computer or a portable device, such as a cellular telephone, a smart phone, a display pager, a radio frequency (RF) device, an infrared (IR) device an Near Field Communication (NFC) device, a Personal Digital Assistant (PDA), a handheld computer, a tablet computer, a phablet, a laptop computer, a set top box, a wearable computer, smart watch, an integrated or distributed device combining various features, such as features of the forgoing devices, or the like.

A computing device may vary in terms of capabilities or features. Claimed subject matter is intended to cover a wide range of potential variations. For example, a smart phone, phablet or tablet may include a numeric keypad or a display of limited functionality, such as a monochrome liquid crystal display (LCD) for displaying text. In contrast, however, as another example, a web-enabled computing device may include one or more physical or virtual keyboards, mass storage, one or more accelerometers, one or more gyroscopes, global positioning system (GPS) or other location-identifying type capability, or a display with a high degree of functionality, such as a touch-sensitive color 2D or 3D display, for example.

A computing device may include or may execute a variety of operating systems, including a personal computer operating system, such as a Windows®, iOS® or Linux®, or a mobile operating system, such as iOS®, Android®, or Windows® Mobile, or the like.

A computing device may include or may execute a variety of possible applications, such as a computing software application enabling communication with other devices, such as communicating one or more messages, such as via email, short message service (SMS), or multimedia message service (MMS), including via a network, such as a social network, to provide only a few possible examples. A computing device may also include or execute an application to communicate content, such as, for example, textual content, multimedia content, or the like. A computing device may also include or execute an application to perform a variety of possible tasks, such as browsing, searching, playing various forms of content, including locally stored or streamed video, or games (such as fantasy sports leagues). The foregoing is provided to illustrate that claimed subject matter is intended to include a wide range of possible features or capabilities.

The storage of the disclosed computing device(s) may include computer readable media in the form of non-permanent memory, random access memory (RAM) and/or non-volatile storage or the like, such as read-only memory (ROM) or flash memory (flash RAM). The storage is an example of computer readable media.

For purposes of this disclosure, the computer-readable media includes permanent and non-permanent, movable and non-movable media that can achieve information storage by means of any methods or techniques. The information may be computer-readable instructions, data structures, program modules or other data. Examples of computer storage media include, but are not limited to, phase-change memory (PRAM), static random access memory (SRAM), dynamic random access memory (DRAM), other types of random access memory (RAM), read-only memory (ROM), electrically erasable programmable read-only memory (EEPROM), flash memory or other memory technologies, read-only compact disc read-only memory (CD-ROM), digital versatile disk (DVD) or other optical storages, magnetic cassette, magnetic tape, magnetic disk storage or other magnetic storage devices, or any other non-transmission media that can be used for storing the information accessible by a computing device. In light of the definitions herein, the computer readable media does not include non-transitory computer readable media, such as modulated data signals and carrier waves.

For the purposes of this disclosure the term "server" should be understood to refer to a service point which provides processing, database, and communication facilities. By way of example, and not limitation, the term "server" can refer to a single, physical processor with associated communications and data storage and database facilities, or it can refer to a networked or clustered complex of processors and associated network and storage devices, as well as operating software and one or more database systems and application software that support the services provided by the server. Servers may vary widely in configuration or capabilities, but generally a server may include one or more central processing units and memory. A server may also include one or more mass storage devices, one or more power supplies, one or more wired or wireless network interfaces, one or more input/output interfaces, or one or more operating systems, such as Windows Server, Mac OS X, Unix, Linux, FreeBSD, or the like.

For the purposes of this disclosure a "network" should be understood to refer to a network that may couple devices so that communications may be exchanged, such as between a server and a computing device or other types of devices, including between wireless devices coupled via a wireless network, for example. A network may also include mass storage, such as network attached storage (NAS), a storage area network (SAN), or other forms of computer or machine readable media, for example. A network may include the Internet, one or more local area networks (LANs), one or more wide area networks (WANs), wire-line type connections, wireless type connections, cellular or any combination thereof. Likewise, sub-networks, which may employ differing architectures or may be compliant or compatible with differing protocols, may interoperate within a larger network. Various types of devices may, for example, be made available to provide an interoperable capability for differing architectures or protocols. As one illustrative example, a router may provide a link between otherwise separate and independent LANs.

A communication link or channel may include, for example, analog telephone lines, such as a twisted wire pair, a coaxial cable, full or fractional digital lines including T1, T2, T3, or T4 type lines, Integrated Services Digital Networks (ISDNs), Digital Subscriber Lines (DSLs), wireless links including satellite links, or other communication links or channels, such as may be known to those skilled in the art. Furthermore, a computing device or other related electronic devices may be remotely coupled to a network, such as via a wired or wireless line or link, for example.

For purposes of this disclosure, a "wireless network" should be understood to couple computing devices with a network. A wireless network may employ stand-alone ad-hoc networks, mesh networks, Wireless LAN (WLAN) networks, cellular networks, or the like. A wireless network may further include a system of terminals, gateways, routers, or the like coupled by wireless radio links, or the like, which may move freely, randomly or organize themselves arbitrarily, such that network topology may change, at times even rapidly.

A wireless network may further employ a plurality of network access technologies, including Long Term Evolution (LTE), WLAN, Wireless Router (WR) mesh, or 2nd, 3rd, or 4th generation (2G, 3G, or 4G) cellular technology, or the like. Network access technologies may enable wide area coverage for devices, such as computing devices with varying degrees of mobility, for example.

For example, a network may enable RF or wireless type communication via one or more network access technologies, such as Global System for Mobile communication (GSM), Universal Mobile Telecommunications System (UMTS), General Packet Radio Services (GPRS), Enhanced Data GSM Environment (EDGE), 3GPP Long Term Evolution (LTE), LTE Advanced, Wideband Code Division Multiple Access (WCDMA), Bluetooth, 802.11b/g/n, or the like. A wireless network may include virtually any type of wireless communication mechanism by which signals may be communicated between devices, such as a computing device, between or within a network, or the like.

Description of Embodiments

Implementation of a non-limiting method in accordance with the present application is further discussed below in accordance with a non-limiting embodiment. As shown in FIG. 1, a flow diagram of a method for calculating a product image obstructed score according to some embodiments of the present application is depicted. In some embodiments, the method referenced in FIG. 1 includes:

S101: acquiring a product image, recording a coordinate of each pixel in the product image, and marking the pixels located at a boundary of the product image as boundary pixels.

Wherein the product image may be the product image displayed by the merchant on the shopping website or other similar images, as it is not specifically limited in this regard.

S102: extracting a first region block in the product image and marking the pixels located at the first region block as the obstructed pixels, wherein the first region block comprises at least one of the following: a text region block, a trademark region block, and a pattern region block.

In some embodiments, the method for extracting the first region block in the product image may be achieved by employing any known or to be known methodology, technology, algorithm, architecture or technique, such as, for example, for the text region block, a method based on texture statistics and a method based on regional analysis or the like may be used.

In some embodiments, in order to facilitate extracting a more accurate first region block, the extracted original first region block may be expanded to obtain the expanded first region block. In some embodiments, the steps of extracting the first region block in the product image and marking the pixels located at the first region block as the obstructed pixels may include:

extracting the first region block in the product image;
analyzing a color saliency of the first region block;
expanding the first region block to obtain the expanded first region block based on magnitude of the color saliency of the first region block; and
marking the pixels located at the expanded first region block as the obstructed pixels.

In some embodiments, the color saliency of the first region block may be obtained by calculating a distance of the first region block from a primary color of the surrounding background, or by calculating a distance of the first region block from a primary color saturation of the surrounding background. The first region block is expanded, the method of which may apply, for example, morphology dilation, wherein a dilation radius is directly proportional to the previously obtained color saliency.

S103: calculating an obstructed cutting space area corresponding to each pixel in the product image based on positional relations of each pixel in the product image with the boundary pixels and with the obstructed pixels.

According to embodiments of the instant disclosure, the obstructed cutting space area refers to an area free of the obstructed pixels around each pixel in the product image after being cut by the first region block. In calculating the obstructed cutting space area corresponding to each pixel in the product image, a variety of methods such as, but not limited to, circular or rectangular manners, for example, may be employed. When the circular manner is employed, each pixel may be used as a center point respectively, and a search is conducted in accordance with the radius from small to large. If the circle area of the radius does not contains boundary pixels or obstructed pixels, the searching continues with an increased radius, and if the circle area of the radius does contain boundary pixels or obstructed pixels, the previous radius is used as a radius for calculating the obstructed cutting space area to obtain the obstructed cutting space area.

Figure 2:
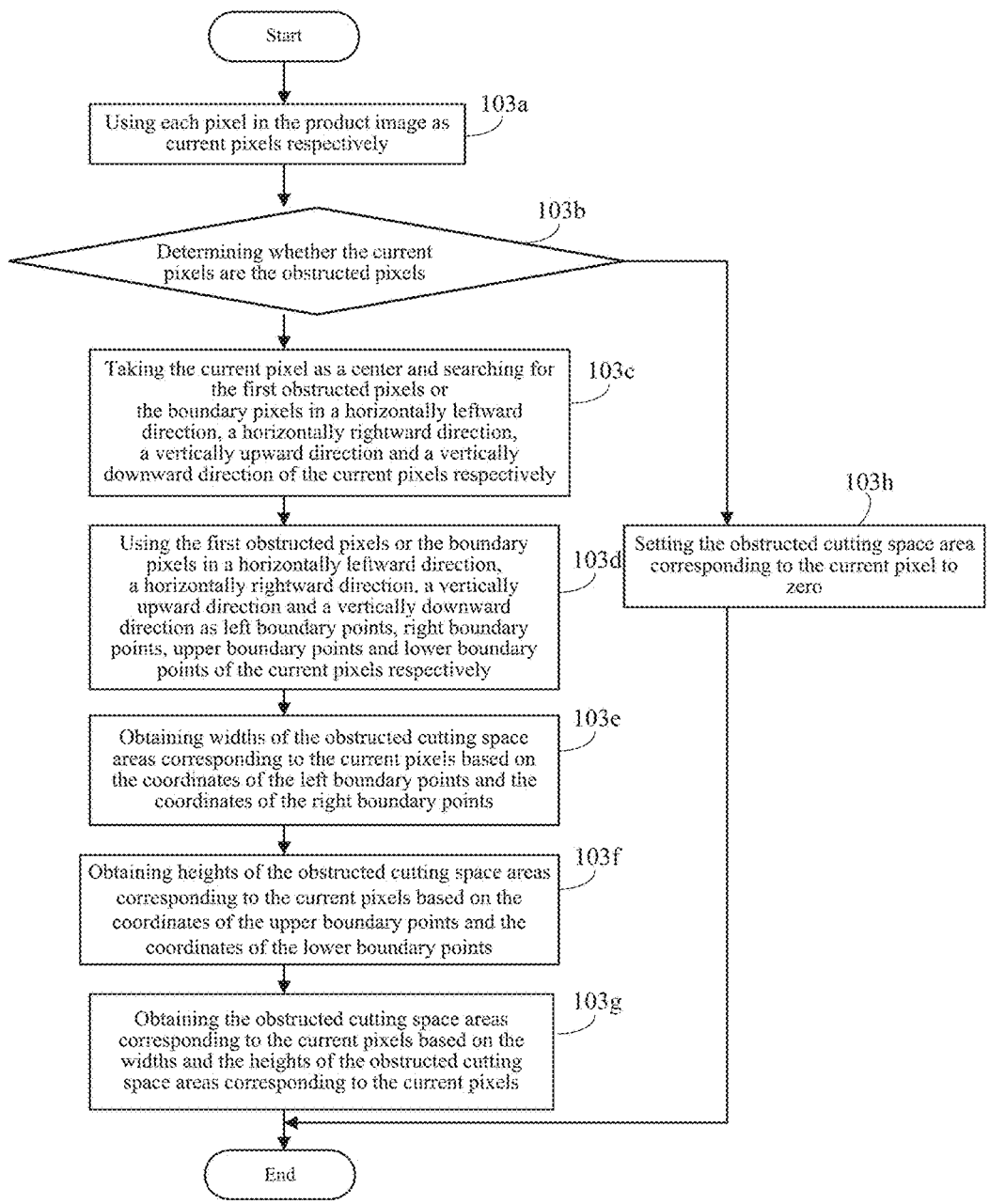
FIG. 2 is a flow diagram of a method for calculating a product image obstruction score according to some embodiments of the present disclosure.

In some embodiments, when the rectangular manner is employed, with reference to FIG. 2, the steps of calculating the obstructed cutting space area corresponding to each pixel in the product image based on positional relations of each pixel in the product image with the boundary pixels and the obstructed pixels may include:

S103a: using each pixel in the product image as current pixels respectively.

S103b: determining whether the current pixels are the obstructed pixels, if not, performing S103c; otherwise, performing S103h.

S103c: taking the current pixel as a center and searching for the first obstructed pixels or the boundary pixels in a horizontally leftward direction, a horizontally rightward direction, a vertically upward direction and a vertically downward direction of the current pixels respectively.

In some embodiments, the first obstructed pixel, for example, taking the first obstructed pixel in the horizontally leftward direction of the current point for illustration, is the first obstructed pixel encountered in searching in the horizontally leftward direction of the current pixel by taking the current pixel as a center, and if no obstructed pixels exist in the horizontally leftward direction of the current pixel, the boundary pixel in the horizontally leftward direction of the current pixel is finally searched. Other directions are similar and thus are not described in more detail herein as a person of skill in the art would understand such disclosure related to the other disclosed directions.

S103d: using the first obstructed pixels or the boundary pixels in a horizontally leftward direction, a horizontally rightward direction, a vertically upward direction and a vertically downward direction as left boundary points, right boundary points, upper boundary points and lower boundary points of the current pixels respectively.

S103e: obtaining widths of the obstructed cutting space areas corresponding to the current pixels based on the coordinates of the left boundary points and the coordinates of the right boundary points.

In some embodiments, a difference between the coordinate of the left boundary point and the coordinate of the right boundary point is the width of the obstructed cutting space area corresponding to the current pixel.

S103f: obtaining heights of the obstructed cutting space areas corresponding to the current pixels based on the coordinates of the upper boundary points and the coordinates of the lower boundary points.

In some embodiments, a difference between the coordinate of the upper boundary point and the coordinate of the lower boundary point is the height of the obstructed cutting space area corresponding to the current pixel.

S103g: obtaining the obstructed cutting space areas corresponding to the current pixels based on the widths and the heights of the obstructed cutting space areas corresponding to the current pixels. The process then ends.

In some embodiments, the width and the height corresponds to the obstructed cutting space area of the current pixel.

S103h: setting the obstructed cutting space area corresponding to the current pixel to zero. The process then ends.

It should be noted that, the present disclosure is not limited to the method described above, any other feasible ways may be employed to achieve the calculation of the obstructed cutting space area corresponding to each pixel in the product image depending on the actual application. For example, each pixel in the product image may be used as the current point respectively, a first obstructed pixel or a boundary pixel is searched in the horizontally leftward direction, horizontally rightward direction, vertically upward direction and vertically downward direction of the current pixel respectively by taking the current pixel as a starting point (i.e., the searching is performed from the current pixel, if the current pixel is the obstructed pixel, the first obstructed pixel or the boundary pixel in the horizontally leftward direction, horizontally rightward direction, vertically upward direction and vertically downward direction is the current pixel, and the corresponding area is zero).

S104: calculating the product image obstructed score based on the obstructed cutting space areas corresponding to all the pixels in the product image.

In some embodiments, the steps of calculating the product image obstructed score based on the obstructed cutting space areas corresponding to all the pixels in the product image include:

using the obstructed cutting space area corresponding to each pixel in the product image or a monotonically increasing function value (e.g., greater than zero) of the obstructed cutting space area corresponding to each pixel as a weight of each pixel in the product image; and calculating the product image obstructed score based on a value obtained by performing weight summation and normalization to all the pixels in the product image.

In some embodiments, the monotonically increasing function (e.g., greater than zero) of the obstructed cutting space area corresponding to each pixel may be, but is not limited to, a squaring function, a square root function, an exponential function, a logarithmic function or the like of the obstructed cutting space area corresponding to each pixel.

In some embodiments, the sum of the weights of all the pixels in the product image is at its maximum when there is no first region block in the product image, where at this time, the obstructed cutting space area corresponding to each pixel in the product image is the area of the product image, and normalization can be performed by dividing the sum of the weights of all the pixels in the product image by the maximum sum of the weights of all the pixels in the product image.

In some embodiments, the steps of calculating the product image obstructed score based on a value obtained by performing weight summation and normalization to all the pixels in the product image include:

using the value obtained by performing weight summation and normalization to all the pixels in the product image as the obstructed reference score of the product image; and obtaining the product image obstructed score based on the obstructed reference score and a preset representation of the obstructed score.

In some embodiments, the value obtained by performing weight summation and normalization to all the pixels in the product image is a decimal, for example, from 0 to 1, and the greater the value is, the less likely the product image is the obstructed image or the less severe the obstruction is. For ease of determination, the value may be used as the obstructed reference score of the product image, and the representation of the obstructed score may be set in a centesimal form (or the like), and the greater the obstructed score is, the more likely the product image includes obstructed portions or the more severe the obstruction is. According to the obstructed reference score and the representation of the obstructed score described above, it can be obtained that the obstructed reference score of 0 corresponds to the obstructed score of 100, the obstructed reference score of 1 corresponds to the obstructed score of 0, the obstructed reference score of 0.1 corresponds to the obstructed score of 90, and the like. Taking the case that the representation of the obstructed score is in a centesimal form, and the greater the obstructed score is, the more likely the product image includes obstruction portions or the more severe the obstruction is.

Figure 3:
FIG. 3 is a schematic diagram of a product image according to some embodiments of the present disclosure.
Figure 4:
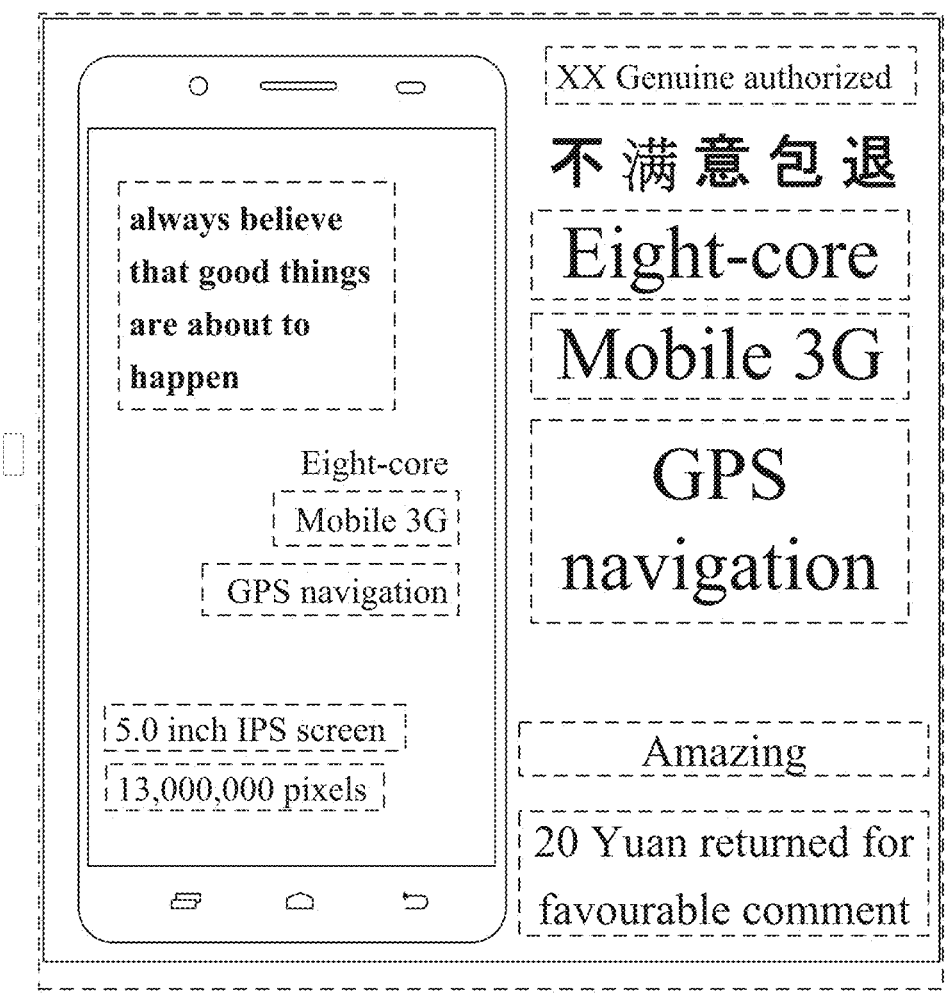
FIG. 4 is a schematic diagram of a first region block in a product image according to some embodiments of the present disclosure.

As a non-limiting example, and referring to FIGS. 3 and 4, the content in the dashed box in FIG. 4 is the first region block extracted from FIG. 3, the obstructed score of FIG. 3 is calculated as 66 in accordance with the method of this embodiment, and FIG. 3 is determined or classified as a moderate obstruction based on the preset determination or classification criteria.

It should be noted that after calculating the product image obstructed score, a corresponding obstructed determination threshold or an obstructed classification threshold can be set according to the meaning of the product image obstructed score (e.g., the greater the obstructed score is, the less likely the product image is the obstructed image or the less severe the obstructed is; or the greater the obstructed score is, the more likely the product image is the obstructed image or the more severe the obstructed is), and the calculated product image obstructed score is compared with the preset obstructed determination threshold or the obstructed classification threshold, and based on the comparison result, the obstructed severity of the product image is determined or classified.

In some embodiments, if the meaning of the obstructed score is that the greater the obstructed score is, the less likely the product image is the obstructed image or the less severe the obstruction is, when the comparison result is that the calculated product image obstructed score is greater than the preset obstructed determination threshold or the obstructed classification threshold, the less likely the product image is the obstructed image or the less severe the obstructed is; and when the comparison result is that the calculated product image obstructed score is less than or equal to the preset obstructed determination threshold or the obstructed classification threshold, the more likely the product image is the obstructed image or the more severe the obstructed is. In some embodiments, if the meaning of the obstructed score is that the greater the obstructed score is, the more likely the product image is the obstructed image or the more severe the obstructed is, then the obstructed severity of the product image is determined or classified based on the comparison result in contrary to the above-described situation, which is not described in detail herein.

By calculating an obstructed cutting space area corresponding to each pixel in the product image based on positional relations of each pixel in the product image with the boundary pixels and the obstructed pixels; and calculating the product image obstructed score based on the obstructed cutting space areas corresponding to all the pixels in the product image (the pixel being an actual element of the product image that can reflect the real condition of the product image), the method for calculating a product image obstructed score described in this embodiment can improve the accuracy of the product image obstructed score, and more accurately determine whether the product image is obstructed, as well as determine the severity of the obstruction. The first region block is expanded to obtain the expanded first region block based on the magnitude of the color saliency of the first region block, such that a more accurate first region block can be obtained, thereby further improving the accuracy of the product image obstructed score.

Figure 5:
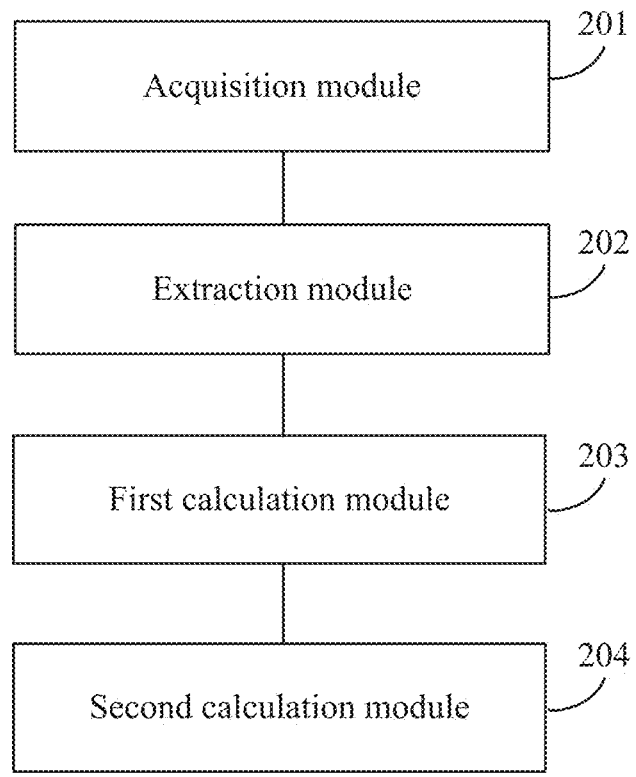
FIG. 5 is a schematic structural diagram of an apparatus for calculating a product image obstruction score according to some embodiments of the present disclosure.

As shown in FIG. 5, a non-limiting structural diagram of an apparatus for calculating a product image obstructed score is depicted. The apparatus includes an acquisition module 201, extraction module 202, first calculation module 203 and a second calculation module 204. It should be understood that the modules discussed herein are non-exhaustive, as additional or fewer modules (or sub-modules) may be applicable to the embodiments of the systems and methods discussed herein. The operations, configurations and functionalities of each module, and their role within embodiments of the present disclosure will be discussed below.

According to some embodiments, the disclosed apparatus includes:

an acquisition module 201, used for acquiring a product image, recording coordinates of each pixel in the product image, and marking the pixels located at a boundary of the product image as boundary pixels;

an extraction module 202, used for extracting a first region block in the product image, and marking the pixels located at the first region block as obstructed pixels;

a first calculation module 203, used for calculating an obstructed cutting space area corresponding to each pixel in the product image based on positional relations of each pixel in the product image with the boundary pixels and the obstructed pixels; and a second calculation module 204, used for calculating the product image obstructed score based on the obstructed cutting space areas corresponding to all the pixels in the product image.

In some embodiments, the extraction module 202 includes:

an extraction unit, used for extracting a first region block in the product image;

an analysis unit, used for analyzing a color saliency of the first region block;

an expansion unit, used for expanding the first region block to obtain the expanded first region block based on magnitude of the color saliency of the first region block; and a marking unit, used for marking the pixels located at the expanded first region block as the obstructed pixels.

In some embodiments, the first calculation module 203 includes:

a first processing unit, used for using each pixel in the product image respectively as a current pixel;

a determination unit, used for determining whether the current pixels are the obstructed pixels;

a searching unit, used for taking the current pixel as a center and searching for the first obstructed pixels or the boundary pixels in a horizontally leftward direction, a horizontally rightward direction, a vertically upward direction and a vertically downward direction of the current pixels respectively, if the current pixels are not the obstructed pixels;

a second processing unit, used for using the first obstructed pixels or the boundary pixels in a horizontally leftward direction, a horizontally rightward direction, a vertically upward direction and a vertically downward direction as left boundary points, right boundary points, upper boundary points and lower boundary points of the current pixels respectively;

a width acquisition unit, used for obtaining widths of the obstructed cutting space areas corresponding to the current pixels based on the coordinates of the left boundary points and the coordinates of the right boundary points;

a height acquisition unit, used for obtaining heights of the obstructed cutting space areas corresponding to the current pixels based on the coordinates of the upper boundary points and the coordinates of the lower boundary points; and an area acquisition unit, used for obtaining the obstructed cutting space areas corresponding to the current pixels based on the widths and the heights of the obstructed cutting space areas corresponding to the current pixels.

In some embodiments, the first calculation module 203 further includes:

a setting unit, used for setting the obstructed cutting space areas corresponding to the current pixels to zero if the current pixels are the obstructed pixels.

In some embodiments, the second calculation module 204 includes:

a weight acquisition unit, used for using the obstructed cutting space area corresponding to each pixel in the product image or a monotonically increasing function value (e.g., greater than zero) of the obstructed cutting space area corresponding to each pixel as a weight of each pixel in the product image; and a score acquisition unit, used for using a value obtained by performing weight summation and normalization to all the pixels in the product image as the product image obstructed score.

In some embodiments, the score acquisition unit includes:

a reference score acquisition unit, used for using the value obtained by performing weight summation and normalization to all the pixels in the product image as the obstructed reference score of the product image; and a score acquisition subunit, used for obtaining the product image obstructed score based on the obstructed reference score and a preset representation of the obstructed score.

In some embodiments, the apparatus further includes:

a comparison module, used for comparing the calculated product image obstructed score with a preset obstructed determination threshold or an obstructed classification threshold; and a determination or classification module, used for determining or classifying an obstructed severity of the product image based on the comparison result.

In some embodiments, the first region block comprises at least one of the following: a text region block, a trademark region block, and a pattern region block.

According to some embodiments, as discussed herein, the apparatus for calculating a product image obstructed score described in reference to FIG. 5 includes: calculating an obstructed cutting space area corresponding to each pixel in the product image based on positional relations of each pixel in the product image with the boundary pixels, and with the obstructed pixels; and calculating the product image obstructed score based on the obstructed cutting space areas corresponding to all the pixels in the product image (the pixel being an actual element of the product image reflecting the real condition of the product image). The application/implementation of such apparatus results in the accuracy of the product image obstructed score being improved over conventional systems, as it can more accurately determine whether a product image is an obstructed image (or contains obstructed portions), along with determining the severity of the obstruction. In some embodiments the first region block is expanded to obtain the expanded first region block based on the color saliency magnitude of the first region block, such that a more accurate first region block can be obtained, thereby further improving the accuracy of the product image obstructed score.

The embodiments of the apparatus discussed above in relation to FIG. 5 correspond to the aforementioned description of the method process, and can therefore be referred to from the description of the method process. As understood by those of skill in the art, details do not need to be repeated herein.

For the purposes of this disclosure a module is a software, hardware, or firmware (or combinations thereof) system, process or functionality, or component thereof, that performs or facilitates the processes, features, and/or functions described herein (with or without human interaction or augmentation). A module can include sub-modules. Software components of a module may be stored on a computer readable medium for execution by a processor. Modules may be integral to one or more servers, or be loaded and executed by one or more servers. One or more modules may be grouped into an engine or an application.

For the purposes of this disclosure the term "user", "subscriber" "consumer" or "customer" should be understood to refer to a consumer of data supplied by a data provider. By way of example, and not limitation, the term "user" or "subscriber" can refer to a person who receives data provided by the data or service provider over the Internet in a browser session, or can refer to an automated software application which receives the data and stores or processes the data.

Those skilled in the art will recognize that the methods and systems of the present disclosure may be implemented in many manners and as such are not to be limited by the foregoing exemplary embodiments and examples. In other words, functional elements being performed by single or multiple components, in various combinations of hardware and software or firmware, and individual functions, may be distributed among software applications at either the client level or server level or both. In this regard, any number of the features of the different embodiments described herein may be combined into single or multiple embodiments, and alternate embodiments having fewer than, or more than, all of the features described herein are possible.

Functionality may also be, in whole or in part, distributed among multiple components, in manners now known or to become known. Thus, myriad software/hardware/firmware combinations are possible in achieving the functions, features, interfaces and preferences described herein. Moreover, the scope of the present disclosure covers conventionally known manners for carrying out the described features and functions and interfaces, as well as those variations and modifications that may be made to the hardware or software or firmware components described herein as would be understood by those skilled in the art now and hereafter.

Several preferred embodiments of the present application are illustrated and described in the aforementioned description, however, as previously described, it is understood that the present application is not intended to be limited to the forms disclosed and is applicable for use in various other combinations, modifications and environments, rather than being considered as excluding other embodiments. Modifications can be made according to the aforementioned teachings or the skills or knowledge in the related art within the scope of the inventive concept, as expressed herein. The modifications and changes made by those skilled in the art should not depart from the spirit and scope of the present application, all of which should be within the extent of protection in the appended claims of the present application.

What is claimed is:

1. A method comprising:

acquiring, by a computing device over a network, a digital image comprising content associated with a product;

analyzing, via the computing device, the digital image, said analysis comprising identifying each pixel in the digital image and recording coordinates of each pixel, said analysis further comprising marking, based on said coordinates the pixels located at a boundary of the digital image as boundary pixels;

extracting, via the computing device based on said analysis, a first region block of pixels in the digital image, said extraction comprising marking the pixels located at the first region block as obstructed pixels;

calculating, via the computing device, an obstructed cutting space area corresponding to each pixel in the digital image, said calculation based on determined positional relations of each pixel in the digital image, the marked boundary pixels and the marked obstructed pixels;

calculating, via the computing device, a digital image obstructed score based on the calculated obstructed cutting space area; and determining, via the computing device, whether to display the digital image based on the digital image obstructed score.

2. The method according to claim 1, wherein the extracting the first region block in the digital image further comprises:

extracting a first region block in the digital image;

analyzing a color saliency of the first region block and determining a color saliency magnitude based on said analysis;

expanding the first region block to obtain the expanded first region block based on the color saliency magnitude of the first region block; and marking the pixels located at the expanded first region block as the obstructed pixels.

3. The method according to claim 1, wherein calculating the obstructed cutting space area further comprises:

using each pixel in the digital image respectively as current pixels;

determining whether the current pixels are the obstructed pixels;

searching, using the current pixel as the center, for the first obstructed pixels or the boundary pixels in a horizontally leftward direction, a horizontally rightward direction, a vertically upward direction and a vertically downward direction of the current pixels respectively, if the current pixels are not the obstructed pixels;

using the first obstructed pixels or the boundary pixels in the horizontally leftward direction, the horizontally rightward direction, the vertically upward direction and the vertically downward direction as left boundary points, right boundary points, upper boundary points, and lower boundary points of the current pixels respectively;

obtaining widths of the obstructed cutting space areas corresponding to the current pixels based on coordinates of the left boundary points and coordinates of the right boundary points;

obtaining heights of the obstructed cutting space areas corresponding to the current pixels based on coordinates of the upper boundary points and coordinates of the lower boundary points; and obtaining the obstructed cutting space areas corresponding to the current pixels based on the widths and the heights of the obstructed cutting space areas corresponding to the current pixels.

4. The method according to claim 3, wherein, after determining whether the current pixels are the obstructed pixels, the method further comprises:

setting the obstructed cutting space areas corresponding to the current pixels to zero if the current pixels are the obstructed pixels.

5. The method according to claim 1, wherein calculating the digital image obstructed score further comprises:

using the obstructed cutting space area corresponding to each pixel in the digital image or a monotonically increasing function value of the obstructed cutting space area corresponding to each pixel as a weight of each pixel in the digital image; and calculating the digital image obstructed score based on a value obtained by performing a weight summation and normalization to all the pixels in the digital image.

6. The method according to claim 5, wherein calculating the digital image obstructed score further comprises:

using the value obtained by performing a weight summation and normalization to all the pixels in the digital image as the obstructed reference score of the digital image; and obtaining the digital image obstructed score based on the obstructed reference score and a preset representation of the obstructed score.

7. The method according to claim 1, wherein after calculating the digital image obstructed score, the method further comprises:

comparing the calculated digital image obstructed score with a preset obstructed determination threshold or a obstructed classification threshold; and determining or classifying a obstructed severity of the digital image based on the comparison result.

8. The method according to claim 1, wherein the first region block comprises at least one of the following: a text region block, a trademark region block, and a pattern region block.

9. A computing device comprising:

a processor;

a non-transitory computer-readable storage medium for tangibly storing thereon program logic for execution by the processor, the program logic comprising:

logic executed by a processor for acquiring, over a network, a digital image comprising content associated with a product;

logic executed by a processor for analyzing the digital image, said analysis comprising identifying each pixel in the digital image and recording coordinates of each pixel, said analysis further comprising marking, based on said coordinates the pixels located at a boundary of the digital image as boundary pixels;

logic executed by a processor for extracting, based on said analysis, a first region block of pixels in the digital image, said extraction comprising marking the pixels located at the first region block as obstructed pixels;

logic executed by a processor for calculating an obstructed cutting space area corresponding to each pixel in the digital image, said calculation based on determined positional relations of each pixel in the digital image, the marked boundary pixels and the marked obstructed pixels;

logic executed by a processor for calculating a digital image obstructed score based on the calculated obstructed cutting space area; and logic executed by the processor for determining whether to display the digital image based on the digital image obstructed score.

10. The computing device according to claim 9, wherein the extracting the first region block in the digital image further comprises:

logic executed by a processor for extracting a first region block in the digital image;

logic executed by a processor for analyzing a color saliency of the first region block and determining a color saliency magnitude based on said analysis;

logic executed by a processor for expanding the first region block to obtain the expanded first region block based on the color saliency magnitude of the first region block; and logic executed by a processor for marking the pixels located at the expanded first region block as the obstructed pixels.

11. The computing device according to claim 9, wherein calculating the obstructed cutting space area further comprises:

logic executed by a processor for using each pixel in the digital image respectively as current pixels;

logic executed by a processor for determining whether the current pixels are the obstructed pixels;

logic executed by a processor for searching, using the current pixel as the center, for the first obstructed pixels or the boundary pixels in a horizontally leftward direction, a horizontally rightward direction, a vertically upward direction and a vertically downward direction of the current pixels respectively, if the current pixels are not the obstructed pixels;

logic executed by a processor for using the first obstructed pixels or the boundary pixels in the horizontally leftward direction, the horizontally rightward direction, the vertically upward direction and the vertically downward direction as left boundary points, right boundary points, upper boundary points, and lower boundary points of the current pixels respectively;

logic executed by a processor for obtaining widths of the obstructed cutting space areas corresponding to the current pixels based on coordinates of the left boundary points and coordinates of the right boundary points;

logic executed by a processor for obtaining heights of the obstructed cutting space areas corresponding to the current pixels based on coordinates of the upper boundary points and coordinates of the lower boundary points; and logic executed by a processor for obtaining the obstructed cutting space areas corresponding to the current pixels based on the widths and the heights of the obstructed cutting space areas corresponding to the current pixels.

12. The computing device according to claim 11, wherein, after determining whether the current pixels are the obstructed pixels, further comprising:

logic executed by a processor for setting the obstructed cutting space areas corresponding to the current pixels to zero if the current pixels are the obstructed pixels.

13. The computing device according to claim 9, wherein calculating the digital image obstructed score further comprises:

logic executed by a processor for using the obstructed cutting space area corresponding to each pixel in the digital image or a monotonically increasing function value of the obstructed cutting space area corresponding to each pixel as a weight of each pixel in the digital image; and logic executed by a processor for calculating the digital image obstructed score based on a value obtained by performing a weight summation and normalization to all the pixels in the digital image.

14. The computing device according to claim 13, wherein calculating the digital image obstructed score further comprises:

logic executed by a processor for using the value obtained by performing a weight summation and normalization to all the pixels in the digital image as the obstructed reference score of the digital image; and logic executed by a processor for obtaining the digital image obstructed score based on the obstructed reference score and a preset representation of the obstructed score.

15. The computing device according to claim 9, wherein after calculating the digital image obstructed score, further comprising:

logic executed by a processor for comparing the calculated digital image obstructed score with a preset obstructed determination threshold or a obstructed classification threshold; and logic executed by a processor for determining or classifying a obstructed severity of the digital image based on the comparison result.

16. The computing device according to claim 9, wherein the first region block comprises at least one of the following: a text region block, a trademark region block, and a pattern region block.

17. A non-transitory computer-readable storage medium tangibly encoded with computer-executable instructions, that when executed by a processor, perform a method comprising:

acquiring, over a network, a digital image comprising content associated with a product;

analyzing the digital image, said analysis comprising identifying each pixel in the digital image and recording coordinates of each pixel, said analysis further comprising marking, based on said coordinates the pixels located at a boundary of the digital image as boundary pixels;

extracting, based on said analysis, a first region block of pixels in the digital image, said extraction comprising marking the pixels located at the first region block as obstructed pixels;

calculating an obstructed cutting space area corresponding to each pixel in the digital image, said calculation based on determined positional relations of each pixel in the digital image, the marked boundary pixels and the marked obstructed pixels;

calculating a digital image obstructed score based on the calculated obstructed cutting space area; and determining whether to display the digital image based on the digital image obstructed score.

18. The non-transitory computer-readable storage medium according to claim 17, wherein the extracting the first region block in the digital image further comprises:

extracting a first region block in the digital image;

analyzing a color saliency of the first region block and determining a color saliency magnitude based on said analysis;

expanding the first region block to obtain the expanded first region block based on the color saliency magnitude of the first region block; and marking the pixels located at the expanded first region block as the obstructed pixels.

19. The non-transitory computer-readable storage medium according to claim 17, further comprising:

using each pixel in the digital image respectively as current pixels;

determining whether the current pixels are the obstructed pixels;

searching, using the current pixel as the center, for the first obstructed pixels or the boundary pixels in a horizontally leftward direction, a horizontally rightward direction, a vertically upward direction and a vertically downward direction of the current pixels respectively, if the current pixels are not the obstructed pixels;

using the first obstructed pixels or the boundary pixels in the horizontally leftward direction, the horizontally rightward direction, the vertically upward direction and the vertically downward direction as left boundary points, right boundary points, upper boundary points, and lower boundary points of the current pixels respectively;

obtaining widths of the obstructed cutting space areas corresponding to the current pixels based on coordinates of the left boundary points and coordinates of the right boundary points;

obtaining heights of the obstructed cutting space areas corresponding to the current pixels based on coordinates of the upper boundary points and coordinates of the lower boundary points; and obtaining the obstructed cutting space areas corresponding to the current pixels based on the widths and the heights of the obstructed cutting space areas corresponding to the current pixels.

\* \* \* \* \*